United States Patent
Hocken et al.

(10) Patent No.: US 10,754,803 B2
(45) Date of Patent: *Aug. 25, 2020

(54) METHODS AND DEVICES THAT UTILIZE HARDWARE TO MOVE BLOCKS OF OPERATING PARAMETER DATA FROM MEMORY TO A REGISTER SET

(71) Applicant: MEDTRONIC, INC., Minneapolis, MN (US)

(72) Inventors: Robert W. Hocken, Scottsdale, AZ (US); Wesley A. Santa, Andover, MN (US); Christopher M. Arnett, Dayton, MN (US); Jalpa S. Shah, Cumming, GA (US); Joel E. Sivula, White Bear Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,905

(22) Filed: Jun. 24, 2019

(65) Prior Publication Data

US 2019/0310955 A1 Oct. 10, 2019

Related U.S. Application Data

(63) Continuation of application No. 15/572,777, filed as application No. PCT/US2016/029626 on Apr. 27, 2016, now Pat. No. 10,339,081.

(Continued)

(51) Int. Cl.
*G11C 16/04* (2006.01)
*G06F 13/28* (2006.01)

(Continued)

(52) U.S. Cl.
CPC .......... *G06F 13/28* (2013.01); *A61N 1/36146* (2013.01); *A61N 1/37235* (2013.01); *G11C 16/12* (2013.01); *H03K 3/64* (2013.01)

(58) Field of Classification Search
CPC .. G06F 13/28; A61N 1/36146; A61N 1/37235
(Continued)

(56) References Cited

U.S. PATENT DOCUMENTS 6,128,528 A * 10/2000 Ericksen .................. A61N 1/37
607/2
10,339,081 B2 7/2019 Hocken

OTHER PUBLICATIONS

U.S. Appl. No. 16/275,545, filed Feb. 14, 2019.

* cited by examiner

*Primary Examiner* — Vu A Le
(74) *Attorney, Agent, or Firm* — Withers & Keys, LLC (57) ABSTRACT

A hardware based block moving controller of an active device such as an implantable medical device that provides electrical stimulation reads a parameter data from a block of memory and then writes the parameter data to a designated register set of a component that performs an active function. The block of memory may include data that specifies a size of the block of memory to be moved to the register set. The block of memory may also include data that indicates a number of triggers to skip before moving a next block of memory to the register set. A trigger that causes the block moving controller to move the data from the block of memory to the register set may be generated in various ways such as through operation of the component having the register set or by a separate timer.

28 Claims, 6 Drawing Sheets

Related U.S. Application Data (60) Provisional application No. 62/159,268, filed on May 9, 2015.

(51) Int. Cl.
  *A61N 1/36* (2006.01)
  *A61N 1/372* (2006.01)
  *G11C 16/12* (2006.01)
  *H03K 3/64* (2006.01)

(58) Field of Classification Search
  USPC .................................................. 365/185.19
  See application file for complete search history.

140# METHODS AND DEVICES THAT UTILIZE HARDWARE TO MOVE BLOCKS OF OPERATING PARAMETER DATA FROM MEMORY TO A REGISTER SET

TECHNICAL FIELD

Embodiments relate to methods and devices that utilize register sets to implement operating parameters. More particularly, embodiments relate to methods and devices that utilize hardware to move blocks of operating parameter data from a memory device to a set of registers.

BACKGROUND

Active devices such as active implantable medical devices that generate electrical stimulation signals utilize a set of registers to hold operating parameter data that is implemented by a given component of the device. For instance, an implantable medical device may include a stimulation engine that creates stimulation waveforms based on waveform parameters that are stored in registers of the stimulation engine.

In order to control the operation of the component, such as a stimulation engine, in many cases the parameter data present in the registers is changed according to a prescribed sequence. For example, for a stimulation engine, the pattern of stimulation pulses may be changed in order to ramp up stimulation amplitudes and then ramp them back down. Other examples include changing the rate and/or pulse width of stimulation pulses, controlling active recharge pulses, and so on.

An active device often utilizes firmware to implement device programming. Firmware is conventionally responsible for changing the operating parameters in the set of registers in order to control the component of interest such as the stimulation engine. However, for circumstances such as controlling the generation of waveforms, the firmware must synchronize the effort to change the parameter values with the operation of the component being controlled so that the changes are able to be implanted by the component at the appropriate time. This creates a significant amount of overhead for the firmware that may overburden the firmware and prevent the firmware from performing other desired functions.

SUMMARY

Embodiments address issues such as these and others by providing a block moving hardware based controller that moves a block of operating parameter data from memory to a set of registers. The block moving hardware based controller receives a trigger that causes the operating parameters to be moved. Each block of data in memory may include data that is indicative of the block size to cause the block moving hardware based controller to move the proper block size to the set of registers. Each block of data in memory may also include data that specifies a number of triggers to skip before moving a next block, such as where the current operating parameters are to be maintained for a particular number of triggering events.

Embodiments provide a method of controlling parameters of an active device. The method involves writing a plurality of block navigation data and corresponding parameter data and address value pairs to locations within a memory device of a block moving hardware-based controller, each block navigation datum and corresponding parameter data and address value pairs defining a block. The method further involves receiving a trigger at the block moving hardware-based controller and in response to receiving the trigger, reading the block navigation datum from the memory device for a first block of the memory device and reading a number of parameter data and address value pairs corresponding to the block navigation datum. The method further involves, upon reading the number of parameter data and address value pairs, writing the parameter data values that have been read from memory to a set of registers corresponding to the address values.

Embodiments provide an active device. The active device includes a block moving hardware based controller comprising a block mover device and a memory device, the block mover having a trigger input. The active device further includes a set of registers, wherein a plurality of block navigation data and corresponding parameter data and address value pairs are present in locations within the memory device, each block navigation datum and corresponding parameter data and address value pairs defining a block. The block mover device receives a trigger, and in response to receiving the trigger, the block mover reads the block navigation datum from the memory device for a first block of the memory device and reads a number of parameter data and address value pairs corresponding to the block navigation datum. The block mover device, upon reading the number of parameter data and address value pairs, writes the parameter data values that have been read from memory to the set of registers corresponding to the address values.

DETAILED DESCRIPTION

Embodiments provide block moving hardware based controllers that receive a trigger to move a block of data from memory to a set of registers. This dedicated hardware based controller maintains synchronization with operations of components being controlled by the data values in the set of registers while relieving other devices such as firmware from moving the data to the registers. The data of a given block may indicate the block size and the hardware based controller may then read block navigation data indicative of block size and move the block of data accordingly. Additionally, the data of a given block may specify a number of triggers to occur before moving the next block of memory.

Figure 1:
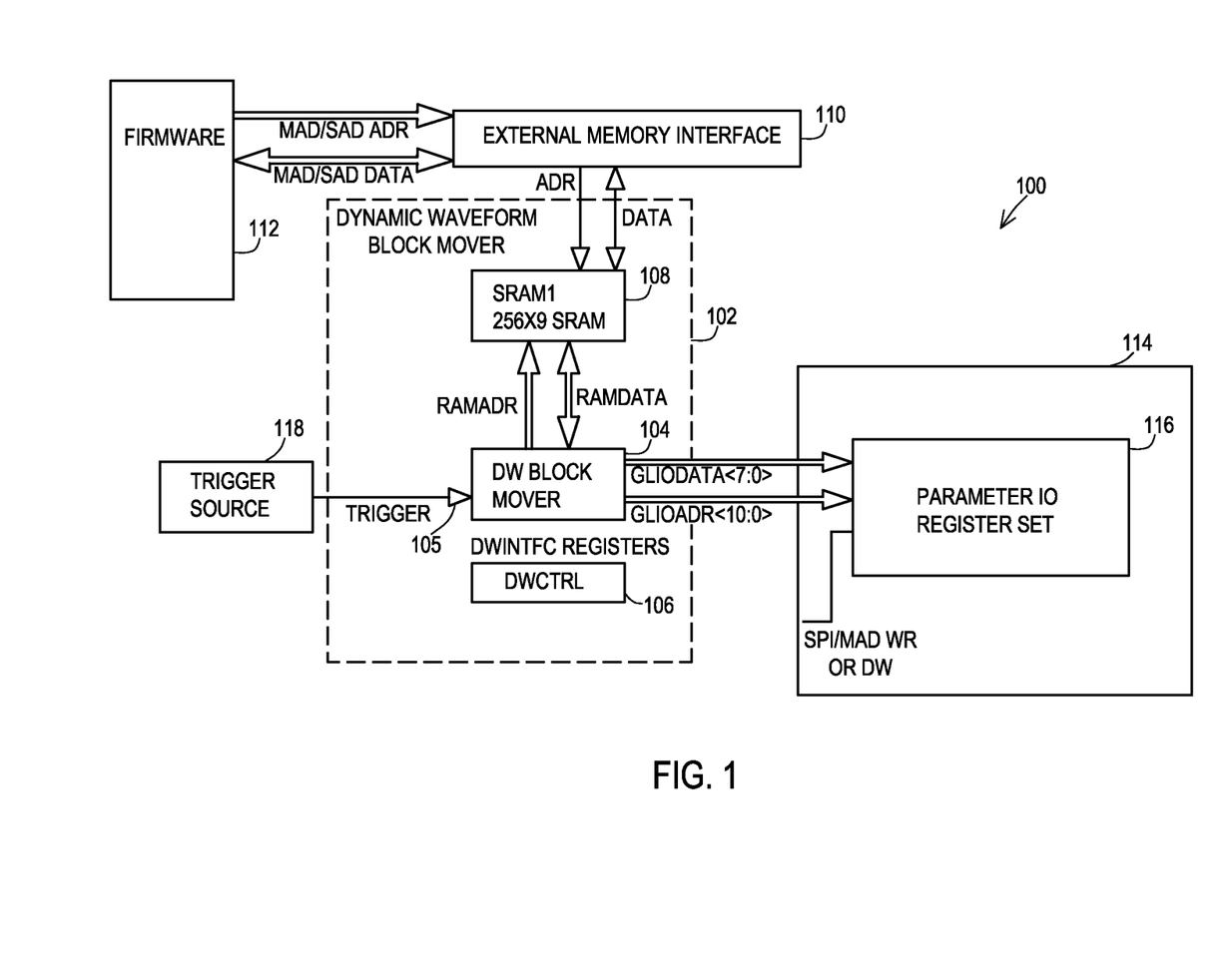
FIG. 1 shows a block diagram of an active device according to various embodiments.

FIG. 1 shows one example of an active device 100 such as an implantable medical device that includes a block moving hardware based controller 102. The controller 102 includes a block mover hardware component 104 that interfaces with a memory device 108 (e.g., SRAM). The block mover hardware component 104 also includes a trigger input 105 and a set of registers 106 that enable the hardware component 104, selects the particular trigger inputs where there are multiple ones present, and selects the memory segments for multiple triggered inputs. Additionally, the block mover hardware component 104 has an interface to a set of registers 116 of a component 114, such as a stimulation engine of an implantable medical device. The controller 102 may be constructed of an application specific integrated circuit, hardwired digital logic, stimulus control, and the like.

The memory device 108 has an external memory interface 110 that allows the memory to be accessed by components external to the controller 102. For instance, a firmware component 112 may write to the memory device 108 via the external memory interface 110 in order to write data to a plurality of memory blocks. Other devices may write to the memory 108 rather than firmware 112, such as an external hardware controller, a programmer, and so forth. In addition to parameter data for controlling the component 114, the data being written to the memory blocks of the memory device 108 may include block navigation data that specifies the block size and interval data that specifies the number of triggers to occur before moving forward with reading and writing the next block of data. The contents of the memory blocks within the memory device 108 are discussed in more detail below with reference to FIG. 3.

A trigger source 118 provides a trigger signal to the trigger input 105 of the block mover hardware component 104. The trigger source may be of various types. For instance, the trigger source may be a timer. As another example, the trigger source 118 may be a trigger output generated by the component 114. For example, the component 114 may be a stimulation engine that behaves as a state machine cunning in a loop where the completion of each loop results in generation of a trigger signal.

Figure 2:
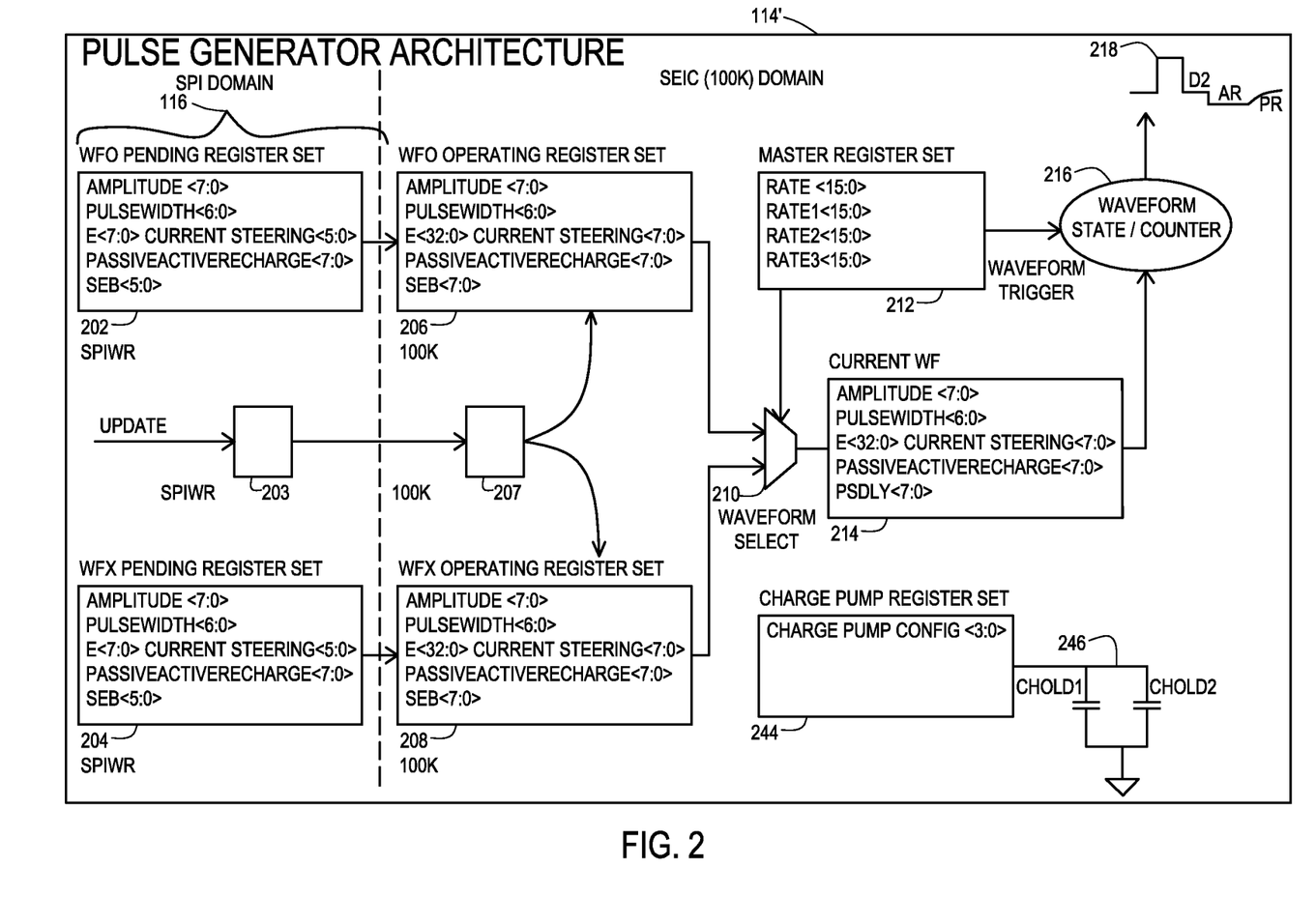
FIG. 2 shows a block diagram of a stimulation engine that is controlled by a set of registers that are programmed to produce a particular waveform according to various embodiments.

FIG. 2 shows an example of such a state machine implementation 114' of the component 114 from FIG. 1. In this example, the component 114' is a waveform generator such as a stimulation engine that produces a one or more electrical pulses per loop. The component 114' includes a first set of waveform parameter registers 202 for a first waveform. Additional sets of pending waveform parameter registers 204 may be included for each additional waveform that may be used during a loop of the state machine. A pending update register 203 may also be included and is discussed further below.

In this example, the component 114' operates one block ahead of the controller 102 by including operating register sets 206, 208 in addition to the pending register sets 202, 204. The operating register sets 206, 208 hold the parameter data that was loaded into the pending register sets 202, 204 in the previous loop. Upon the block moving controller 102 being triggered to move data from the memory 108 to the pending registers 116, a value is also written to the update register 203 by the block moving controller 102 that triggers the component 114' to move the parameter values from the pending register sets 202, 204 to the operating register sets 206, 208 at the next rate interval update trigger. The update register 203, being asserted upon the next rate interval trigger occurring, is represented as update register 207 showing that the update register 207 has resulted in the update of the operating registers 206, 208.

In this example, each output channel of the component 114' has a waveform selector 210 that accesses any one of the operating registers 206, 208 for the particular output channel in order to implement the parameters of a selected waveform to produce the electrical waveform from the output channel. For instance, in an implantable medical device, the waveform selector 210 may choose the particular waveform to be implemented at a given time for a given electrode on an implantable medical lead. The selected waveform is represented in this depiction as a current waveform register 214. The operation of the waveform selector 210 is controlled by a master register set 212. The selected waveform of the current waveform register 214 and the waveform trigger specified by the master register set 212 defines the waveform state and waveform counter of the electrical waveform output 218 of the given output channel. Based on the specified delays between the current pulse and the next pulse, the waveform selector 210 then selects the next waveform register set to cause the next waveform to be output, and so on until the waveform sequence of the sets of registers is complete.

The component 114' of this example that produces an electrical waveform includes a charge pump register set 244. This register set 244 dictates the charging of a bank 246 of hold capacitors that provide the electrical energy to produce each electrical waveform in the series of waveforms. The chare pump operation is not directly related to the block moving controller 102.

Figure 3:
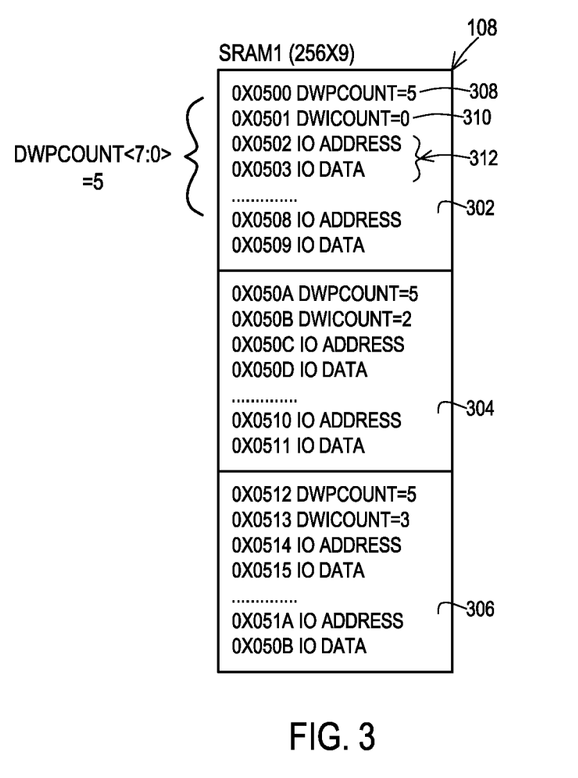
FIG. 3 shows a configuration of memory of an active device according to various embodiments.

FIG. 3 shows an example of how memory blocks are established within the memory device 108 of FIG. 1. Three memory blocks 302, 304, 306 are shown in this example, with each memory block having sequential memory locations. Each memory block may utilize a memory location at a dedicated position within the block, such as the first memory location, that specifies where the next block begins. In this example, each memory block includes a first memory location 308 that provides a block navigation datum to indicate the size of the block by specifying a parameter count that indicates how many pairs of data to read in order to read the entire memory block. In this example, the parameter count is five which indicates that ten memory locations providing five pairings should be read, which includes the pairing that has the count. As another example, the dedicated memory location such as the first memory location 308 may include a block navigation datum that specifies a memory address that indicates where the next block begins. For instance, the memory location may include a block navigation datum that specifies the last address of the current block, such as 0x0509 or specifies the first address of the next block, such as 0x050A, in order to indicate the block size.

Each parameter data pair 312 includes a parameter address value and a parameter data value, where the address value specifies the pending register of register set 116 where the parameter data value should be written. The parameter data value specifies the characteristic of the operation of the component 114, such as a pulse amplitude, pulse width, pulse rate, and so forth where the component 114 generates a waveform. One of the parameter data and address data pairings corresponds to the update data that is moved to the update register 203 as in FIG. 2 to cause the component 114' to move the data in the pending register sets to the operating register sets.

This example also includes a dedicated memory location, such as a second memory location 310, that stores an interval count. In this example, the second memory location is paired with the first memory location 308 that stores the parameter count such that these two memory locations 308, 310 are in a designated location, namely, the first two locations of the block such that the block mover 104 is configured to read these first two memory locations to obtain the parameter and interval counts. The interval count specifies how many triggers should be received by the block mover 104 before reading and writing the next memory block to the pending registers 116. In this example, the memory block 302 specifies that the interval count is zero such that the block mover should not skip any trigger when moving the parameter data of memory block 304. Thus, once the block mover 104 has moved the parameter data of memory block 302 to the pending registers 116, then on the next rate interval block mover trigger, the block mover 104 moves the parameter data of block 304 to the pending registers 116. The memory block 304 specifies an interval count of 2 such that the block mover 104 skips two rater interval block mover triggers before reading the memory block 306 and writing those contents to the pending register set 116.

Figure 4:
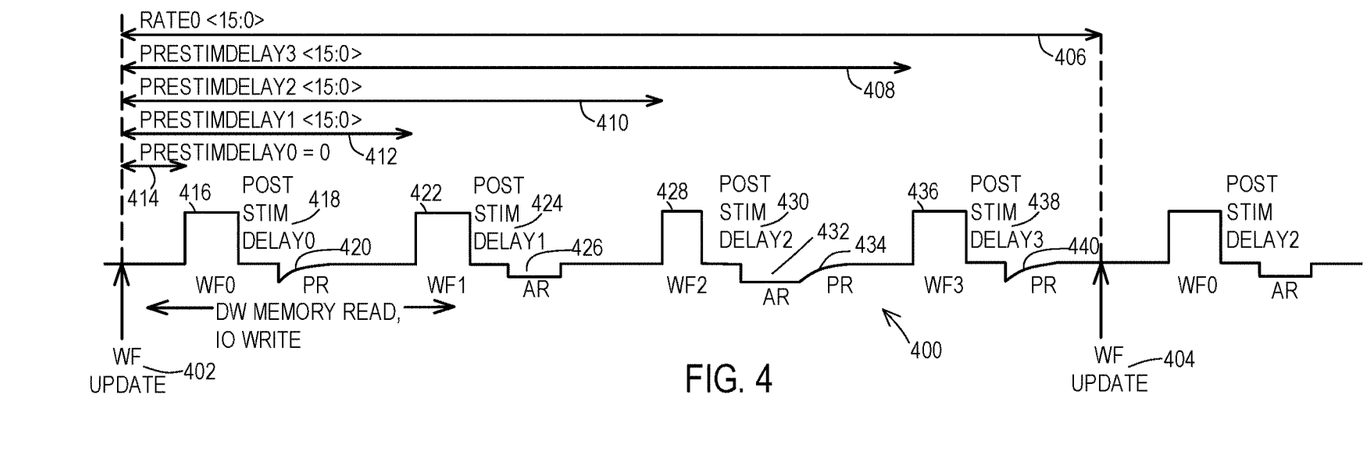
FIG. 4 shows an example of a waveform produced by a component of an active device and shows related parameters that are moved from memory to a set of registers.

FIGS. 4-10 show examples of waveforms formed by a series of individual waveform pulses that may be generated by the active device 100 during a single rate period where parameters of those waveform pulses are specified in the blocks of memory 108 that are ultimately moved by the block mover 104 to the pending register set 116 of the component 114 that produces the waveforms. In FIG. 4, a series of pulses are present for one loop of the waveform state machine through each register set. The timing is such that the operating registers are updated based on the data in the pending registers at a first rate interval update 402, then there are four individual waveform pulses in sequence.

After reaching the end of a first specified delay 414 after the update trigger, the first waveform is produced that has a pulse 416 with a specified amplitude and width, then a specified delay 418, and then a recharge phase 420 which is specified as a passive recharge. Upon completion of a second specified delay 412 after the update trigger, the second waveform is produced that has a pulse 422 with a specified amplitude and width, then a specified delay 424, and then a recharge phase 426 which is specified as an active recharge. Upon completion of a third specified delay 410 after the update trigger, the third waveform is produced that has a pulse 428 with a specified amplitude and width, then a specified delay 430, and then a specified active recharge phase 432 of a given width and then a specified passive recharge phase 434. Upon completion of a fourth specified delay 408 after the update trigger, the fourth and final waveform of this update iteration is produced that has a pulse 436 with a specified amplitude and width, then a specified delay 438, and then a specified passive recharge phase 440.

Upon completion of a rate period 406, an update trigger of a next rate interval is generated that results in a waveform update 404, where pending registers 202, 204 are written to operating registers 206, 208. Parameter data in memory 108 is then written to the pending registers 206, 208 by the block mover 104 during this next rate interval at the appropriate block mover trigger, which may be the same as the trigger of the next rate interval such as WF0 or may be another trigger during the interval.

Relating FIGS. 2, 3, and 4, one example of an implementation may utilize four waveform registers WF0-WF3, each waveform register describing a single pulse plus recharge as shown in FIG. 4. Thus, for a single rate interval 406, each waveform register produces a pulse and recharge for a total of four pulses and recharges. Likewise, the pending register set 116 and operating register set includes the four individual waveform registers. The memory blocks may then specify one or more parameter values per waveform. For instance, each data location and address location pair 312 in memory block 302 may specify a parameter value and register location for each waveform register WF0-WF3. For instance, the block 302 may specify a pulse amplitude for each waveform, where the amplitude may be the same, as shown in FIG. 4, or may ramp upward as discussed in more detail below in relation to FIG. 5.

Any one of the waveforms WF0-WF3 may serve as the trigger source 118 of FIG. 1 for the block moving component 104. Thus, at some point within the rate interval 406, the block mover 104 moves the data from the memory 108 to the pending registers. Then at the end of the rate interval 406, the component 114 updates the operating register set with the data from the pending register set 116 that was moved to the pending register set 116 by the block moving component 104.

Figure 5:
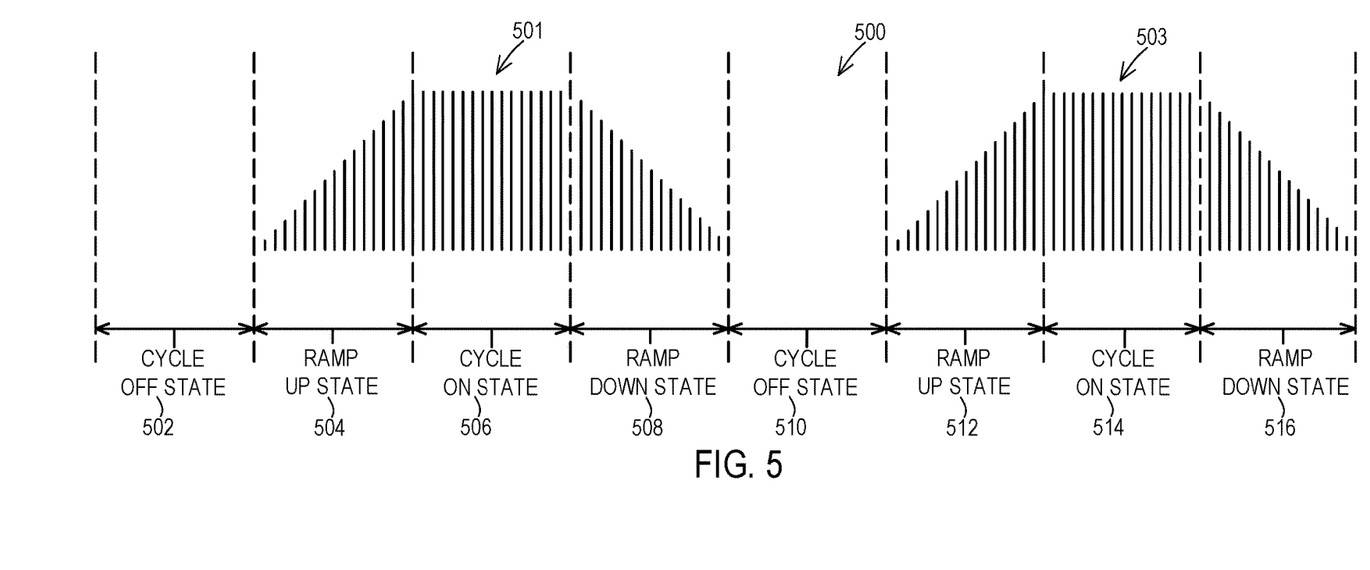
FIG. 5 shows another example of a waveform produced by a component of an active device where the amplitude ramps up and ramps down.

FIG. 5 shows an example 500 where the active device 100 provides a soft start and a soft stop form of stimulation. Here, after a cycle off state 502 ends, the multi-pulse waveform 501 is produced by gradually increasing pulses in specified amplitude during a ramp-up state 504 until reaching a maximum during a cycle on state 506. After completing the maximum amplitude pulses a specified number of times, a parameter can be written to initiate an interrupt, alerting firmware to the completion of the ramp up to the final amplitude. This can be repeated for the ramp down where the waveform 501 begins gradually decreasing the pulse amplitude at a ramp down state 508 until reaching a cycle off state 510. After the specified cycle off state 510, the process may repeat for a subsequent multi-pulse waveform 503 with a ramp up state 512, cycle on state 514, and ramp down state 516. The update trigger may occur after any number of these ramp up/down sequences to alter the multi-pulse waveform.

Figure 6:
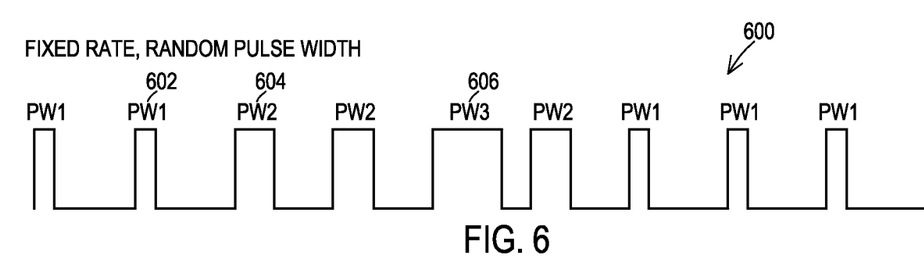
FIG. 6 shows another example of a waveform produced by a component of an active device where there is a fixed rate and amplitude but random pulse width.

FIG. 6 shows an example 600 where the active device 100 provides a specified fixed rate and amplitude of pulses but with random pulse widths for a multi-pulse waveform. In this example, there is a specified common pulse amplitude but a specified first pulse width 602, specified second pulse width 604, and specified third pulse width 606. The waveform selector may operate to select the individual waveform pulses from the operating register sets in a random order to produce the random pulse width pulse train as shown.

Figure 7:
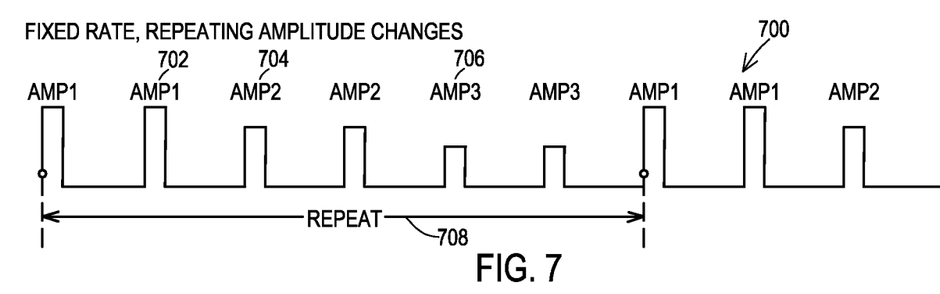
FIG. 7 shows another example of a waveform produced by a component of an active device where there is a fixed rate and pulse width but repeating amplitude changes.

FIG. 7 shows an example 700 where the active device 100 provides a specified fixed rate and pulse width of pulses but with specified repeating amplitude changes. This example is a ramping down of amplitude, where there are two pulses at a specified maximum amplitude 702, then two pulses of a specified lower amplitude 704, and then two final pulses of the lowest specified amplitude 706. This set of serial waveforms 708 may then repeat for some specified number of triggers. The amplitude changes could instead be a ramping up of amplitude in other examples.

Figure 8:
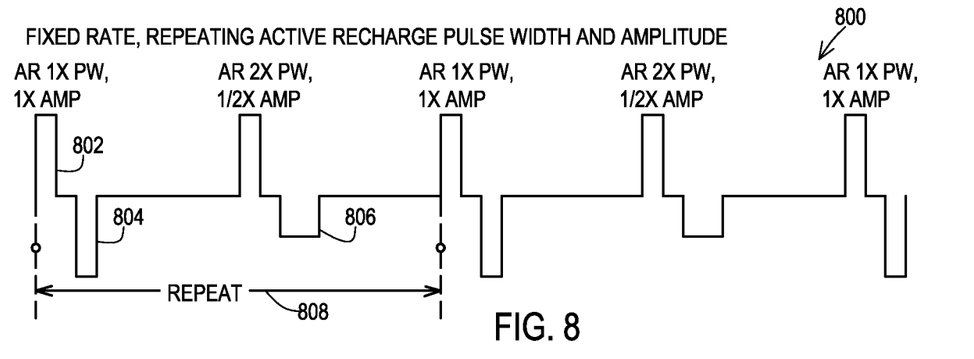
FIG. 8 shows another example of a waveform produced by a component of an active device where there is a fixed rate but an active recharge phase with repeating pulse width and amplitude changes.

FIG. 8 shows an example 800 where the active device 100 provides a specified fixed rate, amplitude, and pulse width but with a repeating change to an active recharge pulse width and amplitude. For each pulse 802, there is an active recharge pulse of opposite polarity. For the first instance of the pulse 802, there is an active recharge pulse 804 that has an equal but opposite amplitude and an equal pulse width to the pulse 802. For the second instance of the pulse 802, there is an active recharge pulse 806 that has a smaller amplitude but larger pulse width. This set of serial waveforms 808 may then repeat for some specified number of triggers.

Figure 9:
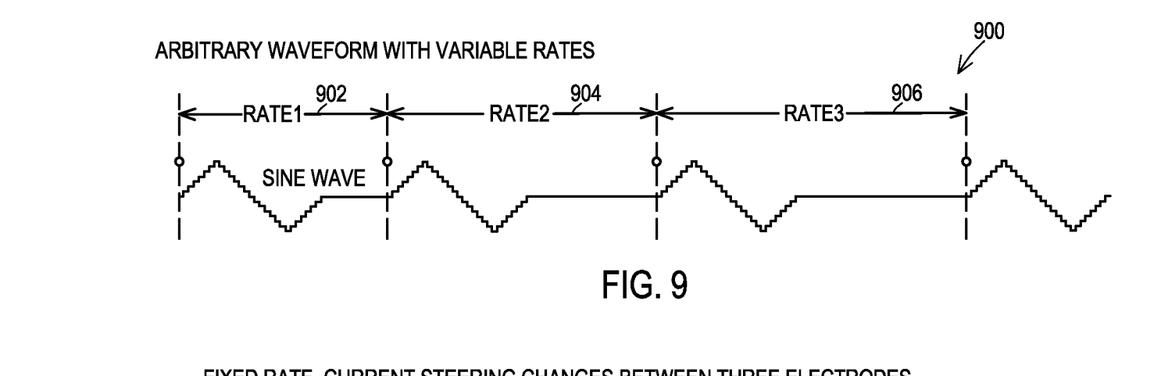
FIG. 9 shows another example of a waveform produced by a component of an active device where there is a varying rate.

FIG. 9 shows an example 900 where the active device 100 provides some waveform shape, in this case a rudimentary sine wave, but with variable rates to each successive waveform. In this example, a first specified waveform rate 902 is the shortest, a second specified waveform rate 904 is longer, and a third specified waveform rate 906 is longest. The waveforms of these three rates 902, 904, 906 may then repeat for some specified number of triggers.

Figure 10:
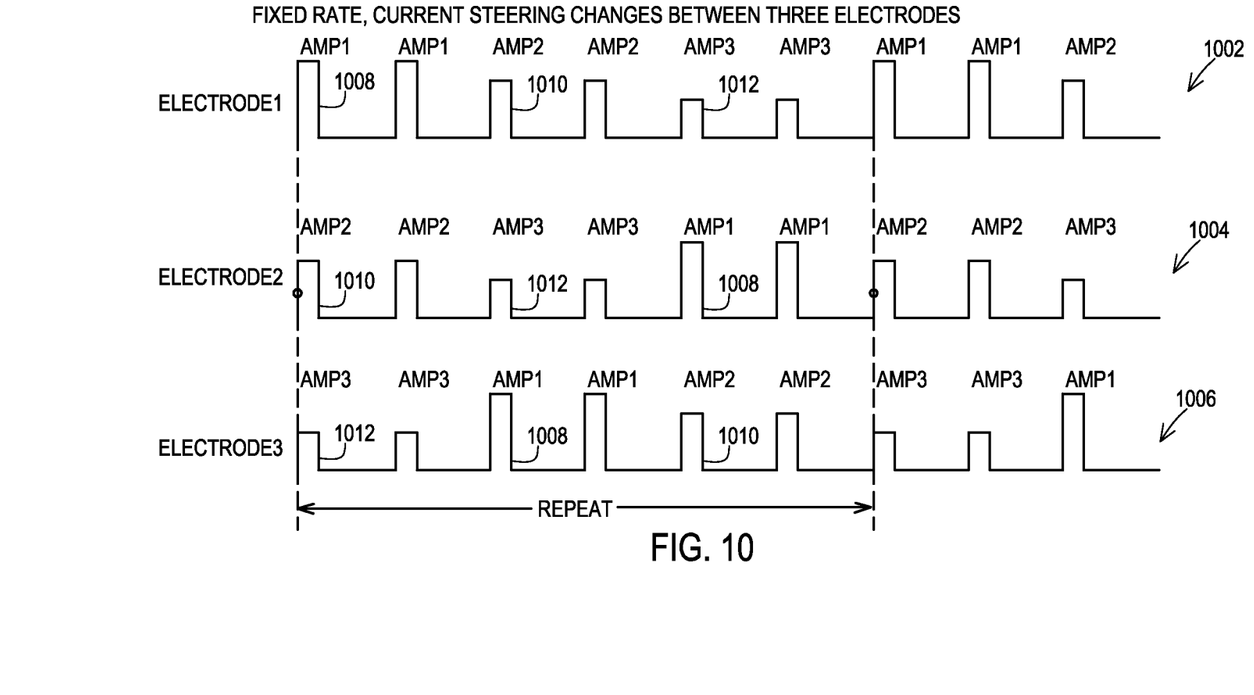
FIG. 10 shows another example of simultaneous a waveforms produced by a component of an active device where there is a fixed rate but amplitude differences between the waveforms to give a current steering effect.

FIG. 10 shows an example 1000 of three simultaneous multi-pulse waveforms 1002, 1004, and 1006. Each waveform 1002, 1004, and 1006 is for each of three electrodes of an implantable medical lead of the active device 100, and hence there is one waveform for each corresponding channel of a multi-channel component 114 of the active device 100. These three waveforms 1002, 1004, and 1006 utilize a common pulse width and rate. However, there are three amplitudes 1008, 1010, and 1012 that are present in the three waveforms 1002, 1004, and 1006, and each waveform has a different amplitude than the other two at any given time. This creates a current steering effect for the stimulation therapy being provided by the three corresponding electrodes.

While embodiments have been particularly shown and described, it will be understood by those skilled in the art that various other changes in the form and details may be made therein without departing from the spirit and scope of the invention.

What is claimed is:

1. A method of controlling parameters of an active device, comprising:
   providing a memory device of a block moving hardware-based controller containing a plurality of block navigation data and corresponding parameter data and address value pairs in memory locations of the memory device, each block navigation datum and corresponding parameter data and address value pairs defining a block, each block navigation datum being positioned within a dedicated block navigation datum location of each corresponding block;
   receiving a trigger at the block moving hardware-based controller;
   in response to receiving the trigger, reading the block navigation datum from the dedicated block navigation datum location of a current block within the memory device and reading a number of parameter data and address value pairs corresponding to the block navigation datum read from the dedicated block navigation datum location; and
   upon reading the number of parameter data and address value pairs, writing the parameter data values that have been read from memory to a set of registers corresponding to the address values.

2. The method of claim 1, further comprising:
   providing the memory device with an interval count at a dedicated interval count location within each block of the memory device;
   receiving additional triggers; and
   once the number of triggers that have been received since writing the parameter data values to the set of registers exceeds the interval count of the current block, then reading a next block navigation datum from the dedicated block navigation datum location of a next block that follows the current memory block in the memory device and reading a next number of parameter data and address value pairs from the next block corresponding to the block navigation datum of the next block; and
   upon reading the next number of parameter data and address value pairs from the next block, writing the next parameter data values that have been read from the next block in memory in response to receiving the trigger to the set of registers corresponding to the address values of the next block.

3. The method of claim 1, wherein the set of registers are a pending set of registers and where the device implements parameters from an operating set of registers, the method further comprising:
   reading an update parameter data and address value pair from the current memory block that causes transfer of parameter values from the pending set of registers to the operating set of registers; and
   writing the update parameter data and address value pair to the pending set of registers to trigger the active device to transfer the parameter data and address value pairs from the pending set of registers to the operating set of registers at a start of a next interval.

4. The method of claim 1, wherein providing the memory device with the plurality of block navigation data and corresponding parameter data and address value pairs to locations within the memory device comprises performing a write operation by a firmware-based device.

5. The method of claim 1, wherein the active device is an implantable medical device.

6. The method of claim 5, wherein the parameter data values define a stimulation waveform of the implantable medical device.

7. The method of claim 6, wherein the parameter data values define ramping and cycling for a stimulation waveform.

8. The method of claim 6, wherein the parameter data values define a random pulse width for a stimulation waveform.

9. The method of claim 6, wherein the parameter data values define a repeating amplitude change for a stimulation waveform.

10. The method of claim 6, wherein the parameter data values define a repeating active recharge pulse width and amplitude change for a stimulation waveform.

11. The method of claim 6, wherein the parameter data values define a rate change for a stimulation waveform.

12. The method of claim 6, wherein the parameter data values define a field steering effect for a set of stimulation waveforms corresponding to a set of stimulation electrodes.

13. The method of claim 1, wherein the block navigation datum of each block is a parameter count defining the number of parameter and address data pairs are contained within the memory block containing the parameter count.

14. The method of claim 1, wherein the block navigation datum of each block is a memory location address of the memory device.

15. An active device, comprising:
a block moving hardware based controller comprising a block mover device and a memory device, the block mover having a trigger input;
a set of registers, wherein a plurality of block navigation data and corresponding parameter data and address value pairs are present in locations within the memory device, each block navigation datum and corresponding parameter data and address value pairs defining a block, each block navigation datum being positioned within a dedicated block navigation datum location of each corresponding block, wherein the block mover receives a trigger, and in response to receiving the trigger, the block mover reads the block navigation datum from the dedicated block navigation datum location of a current block within the memory device and reads a number of parameter data and address value pairs corresponding to the block navigation datum read from the dedicated block navigation datum location, and the block mover upon reading the number of parameter data and address value pairs, writes the parameter data values that have been read from memory to the set of registers corresponding to the address values.

16. The active device of claim 15, wherein an interval count is present within a dedicated interval count location within each block of the memory device, wherein the block moving hardware based controller receives additional triggers and once the number of triggers that have been received since writing the parameter data values to the set of registers exceeds the interval count of the current block, then reading a next block navigation datum and reading a next number of parameter data and address value pairs corresponding to the next block navigation datum for a next block that follows the current memory block in the memory device, and upon reading the next number of parameter data and address value pairs from the next block, the block moving hardware based controller writes the next parameter data values that have been read from the next block in memory in response to receiving the trigger to a set of registers corresponding to the address values of the next block at a start of a next interval.

17. The active device of claim 15, wherein the set of registers are a pending set of registers, the active device further comprising an operating set of registers, wherein the active device implements parameters from the operating set of registers, and wherein the block moving hardware based controller reads an update parameter data and address value pair from the current memory block that causes transfer of parameter values from the pending set of registers to the operating set of registers and writes the update parameter data and address value pair to the pending set of registers to trigger the active device to transfer the parameter data and address value pairs from the pending set of registers to the operating set of registers.

18. The active device of claim 15, further comprising a firmware based device that writes the plurality of block navigation data and corresponding parameter data and address value pairs to sequential locations within the memory device.

19. The active device of claim 15, wherein the active device is an implantable medical device.

20. The active device of claim 19, wherein the parameter data values define a stimulation waveform of the implantable medical device.

21. The active device of claim 20, wherein the parameter data values define ramping and cycling for a stimulation waveform.

22. The active device of claim 20, wherein the parameter data values define a random pulse width for a stimulation waveform.

23. The active device of claim 20, wherein the parameter data values define a repeating amplitude change for a stimulation waveform.

24. The active device of claim 20, wherein the parameter data values define a repeating active recharge pulse width and amplitude change for a stimulation waveform.

25. The active device of claim 20, wherein the parameter data values define a rate change for a stimulation waveform.

26. The active device of claim 20, wherein the parameter data values define a field steering effect for a set of stimulation waveforms corresponding to a set of stimulation electrodes.

27. The active device of claim 15, wherein the block navigation datum is a parameter count defining the number of parameter and address data pairs are contained within the memory block containing the parameter count.

28. The active device of claim 15, wherein the block navigation datum of each block is a memory location address within the memory device.

\* \* \* \* \*